United States Patent [19]
Hess et al.

[11] Patent Number: 6,058,326
[45] Date of Patent: May 2, 2000

[54] METHOD AND APPARATUS FOR CARDIAC PACING IN ACCORDANCE WITH MULTIPLE PACING THERAPY FEATURES

[75] Inventors: Michael F. Hess, Minneapolis; Carleen J. Juran, Shoreview, both of Minn.

[73] Assignee: Medtronic, Inc., Minneapolis, Minn.

[21] Appl. No.: 08/920,499

[22] Filed: Aug. 29, 1997

[51] Int. Cl.⁷ .................................................. A61N 1/362
[52] U.S. Cl. ............................................................ 607/9
[58] Field of Search .................................... 607/9, 18

[56] References Cited

U.S. PATENT DOCUMENTS 5,545,186   8/1996   Olson et al. ............................... 607/9

*Primary Examiner*—William E. Kamm
*Assistant Examiner*—George R. Evanisko
*Attorney, Agent, or Firm*—Harold R. Patton; Reed A. Duthler

[57] ABSTRACT

A method and apparatus for the simultaneous administration of multiple pacing therapies in which two or more pacing features which operate to cause the dynamic adjustment of a common operational parameter of a pacing system are activatable at the same time. In one embodiment, a prioritization among multiple pacing features is established, such that when two (or more) features which operate to cause adjustment of a common operational parameter, a lower-priority feature will not override an adjustment made by any higher-priority feature.

26 Claims, 6 Drawing Sheets

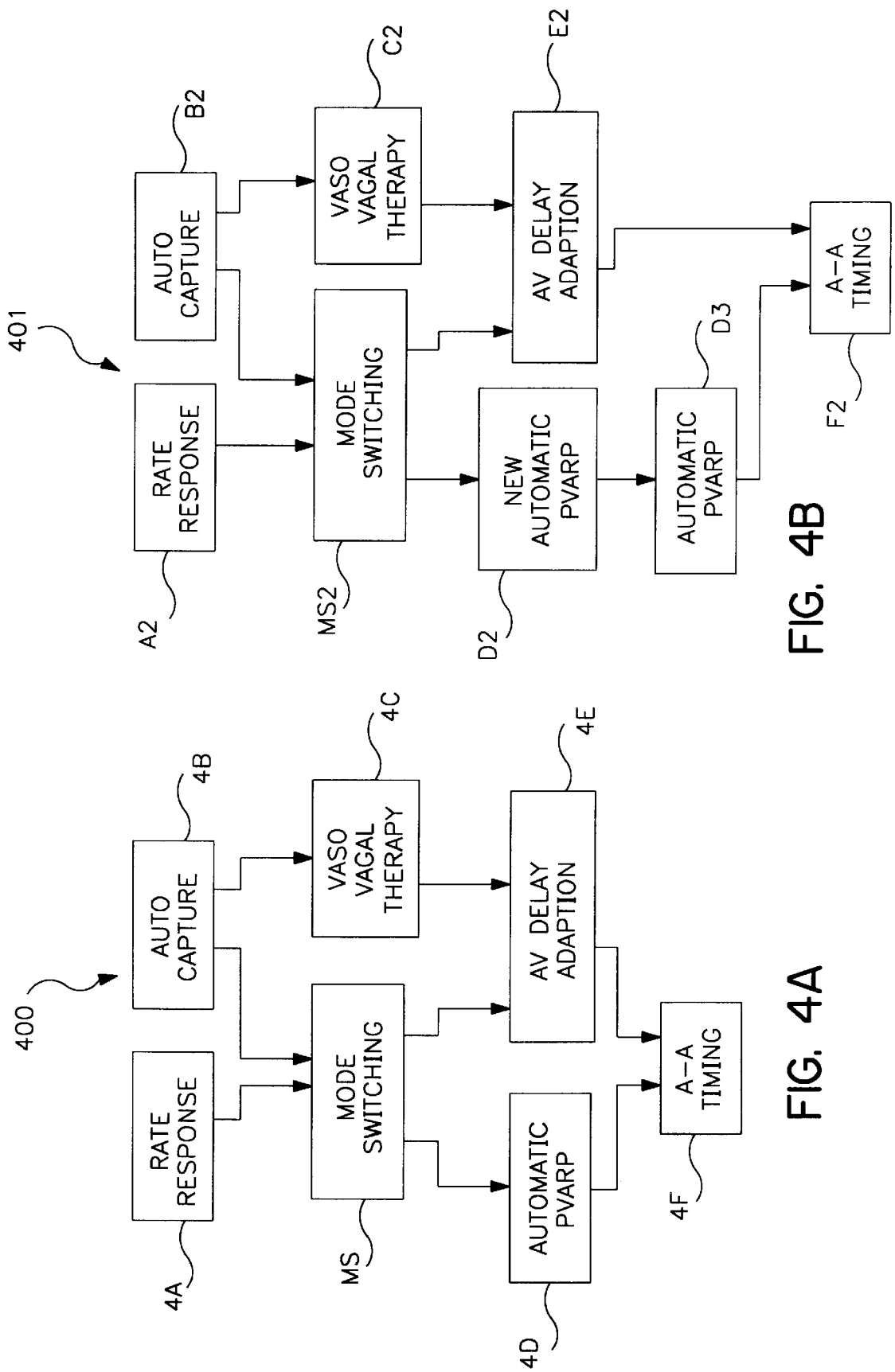

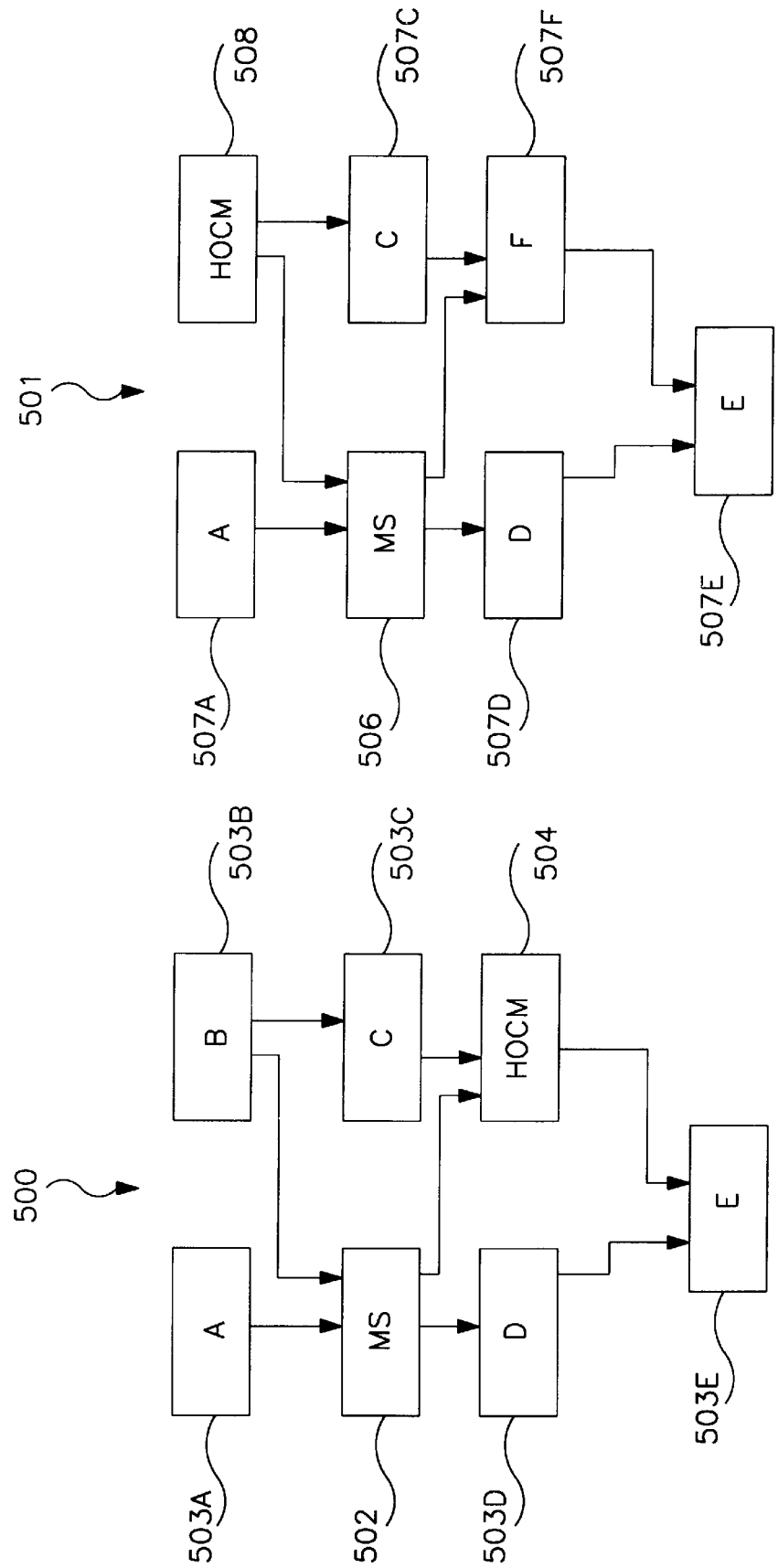

METHOD AND APPARATUS FOR CARDIAC PACING IN ACCORDANCE WITH MULTIPLE PACING THERAPY FEATURES

FIELD OF THE INVENTION

This invention relates generally to automatic, body-implantable medical devices and relates more particularly to a method and apparatus for electrical cardiac stimulation.

BACKGROUND OF THE INVENTION

Many different types of body-implantable, automatic cardiac pulse generator systems, sometimes referred to as "pacemakers,' are known and commercially-available. In general, cardiac pulse generators are devices used to supplant some or all of a malfunctioning heart's natural pacing function. Cardiac pulse generators are typically coupled to a patient's heart via one or more conductive leads. for communicating cardiac stimulating pulses from the pulse generator to the heart, and for conveying sensed cardiac electrical signals to sensing circuitry associated with the pulse generator.

Over the years, the functional capabilities and complexities of cardiac pulse generator systems have increased dramatically. Early body implantable cardiac stimulating devices were fixed-rate, non-inhibited pulse generators which operated to deliver electrical stimulating pulses to the patient's heart at regular intervals, without sensing of, and hence without regard to, intrinsic cardiac electrical activity.

Later, so-called "demand" pacemakers were developed. Demand pacemakers include sensing circuitry for monitoring intrinsic cardiac activity, so that the pulse generator can be inhibited on a beat-to-beat basis, i.e., prevented from delivering stimulating pulses when the heart is functioning properly.

A further development in pulse generator functionality involved variable rate stimulation. Variable rate pulse generators can include means for sensing certain physiologic conditions of the patient e,g, blood oxygenation levels, activity levels and the like, such that the rate at which pacing pulses are delivered can be dynamically varied in accordance with the patient's physiologic demand.

Advances in electronics and semicondonductor technology over the years have been such that it has become increasingly possible and practical to make "multiprogrammable" implantable pulse generators i.e. pulse generators capable of being programmed to operate in any one of a plurality of different operational modes, and to operate with numerous optional diagnostic and therapeutic features. Such features are typically capable of being activated or deactivated as desired, as will be hereinafter discussed in further detail. Multiprogrammable pulse generators are capable of selectively operating in accordance with any of a plurality of pacing algorithms or pacing "modes."

The Elite II™ Models 7084, 7085, and 7086, commercially-available from Medtronic, Inc., Minneapolis, Minn. (assignee of the present invention) are good examples of state-of-the-art multiprogrammable implantable pacemakers. The Elite II™ pacemakers are operable in any one of the following modes (where, in each case, the first letter identifies either a single-chamber (S), dual-chamber (D) or neither-chamber (O) mode, the second letter corresponds to the chamber(s) sensed, the third letter identifies the pacemaker's response to a sensed event—either triggered (T), inhibited (I) or dual (D), and the fourth letter, if any, indicates a rate responsive feature): DDR, DDD, DDIR, DDI, DVIR, DVI, SSIR, SSI, DOOR, DOO, SOOR, and ODO.

The Elite II™ pacemakers have numerous physician-programmable parameters, as set forth in the following Table 1 and maybe considered typical of some cardiac pacemaker programmable parameters. Current version's of pacemakers generally have more such parameters but Table 1 contains a good heuristic set.

TABLE 1

PROGRAMMABLE RANGE OF PARAMETER PROGRAMMABILITY

| | |
| --- | --- |
| Activity Threshold | Low to High, in five settings |
| Rate Responsive | 1 to 10 |
| Acceleration Time | 0.25, 0.5, or 1.0 minutes |
| Declaration Time | 2.5, 5, or 10 minutes |
| Lower Rate in rate responsive modes | 40–90 PPM |
| Lower Rate in other modes | 30–130 PPM |
| Upper Tracking Rate (atrial tracking) | 80–180 PPM |
| Upper Activity Rate (sensor tracking) | 80–180 PPM |
| Temporary Rate | 30–400 PPM |
| Pulse Width | 0.06–1.5 mSec |
| Pulse Amplitude | 0.8–5.0 V |
| Atrial Sensitivity | 0.54.0 mV |
| Ventricular Sensitivity | 1.5–9.0 mV |
| A-V Delay after A-pace (PAV) | 30–350 mSec |
| A-V Delay after A-sense (SAV) | 30–350 mSec |
| Rate Adaptive A-V Delay | On or Off |
| Post-Ventricular Atrial Refractory Period (PVARP) | 160–500 mSec |
| Atrial Refractory Period (ARP) | 160–470 mSec |
| Atrial Blanking Period | 20–40 mSec |
| Ventricular Safety Blanking | 20–40 mSec |
| Pacing Polarity | Unipolar or Bipolar |
| Sensing Polarity | Unipolar of Bipolar |
| Temporary Inhibit | On or Off |

For a given operational mode, and given a desired set of programmed parameter values, there may in addition be selectively activatable features that are provided to enhance the therapeutic benefit of the pacemaker system. Such features, when activated, may function, for example, to dynamically (e.g. on a cycle-to-cycle basis) adjust a programmed parameter value under certain predefined circumstances or in response to the occurrence of certain predefined combinations of events. One well-known example of such a feature is a Rate Response feature, which operates to adjust the base pacing rate parameter for a pacemaker in accordance with a Rate Responsive function applied to the output of an activity sensor.

Ranges and rates of the various rates and parameters will of course be specific to each pacemaker product, as will the kind and number of variable parameters used in each such product. For example, there is no parameter related to what information to output through and responsive to telemetric communication for example, nor is there any parameter having to do with the type of rate smoothing to apply, whether to sense for vasovagal syncopy and so on. The parameter types which could conceivably be employed and adjusted through the mechanism for adjusting table 1's parameters will be apparent to one of ordinary skill in this art.

Programmable operational parameters such as those listed in Table 1 are used by a pacemaker's control circuitry (e.g. , a custom microprocessor or the like) in order to cause the pacemaker to operate in accordance with pacing algorithm. That is, the mode selected (e.g., DDD, DDI, etc . . . ), along with the programmed parameters (e.g., SAV, PAV, PVARP, etc. [These acronyms are defined in the table and previous pages]) and selected features, described as therapy features below define a pacing algorithm or machine state which determines the pacemaker's operational behavior.

The Elite II™ pacemakers, and more state-of-the-art implantable pulse generators, are provided with a telemetry system for facilitating non-invasive programming of the implanted device's operational modes, programmable parameters, and for control of various selectable diagnostic functions, such as those noted above. An external programming unit, such as the Model 9790 Programmer commercially-available from Medtronic, Inc., communicates with the implanted device via radio-frequency signals. Implantable device telemetry systems for facilitating bi-directional communication between an implanted device and an external programming unit are well-known in the art. The telemetry system enables a clinician, using an external programming unit, to program desired values for the various programmable operational parameters, to activate and deactivate the various optional pacing therapy features supported by the implant, and to perform various diagnostic procedures.

Those of ordinary skill in the art will appreciate that for state-of-the-art multiprogrammable pacemaker systems capable of performing numerous different complex operations, often decisions and trade-offs must be made in connection with the selection or activation of various features, modes of operation, and programmed parameter values. In the prior art, many such decisions and trade-offs are commonly made at the programmer-interface level, i.e., during programming of the device at the pacemaker clinic by the doctor operating a programmer. From the programming clinician's standpoint, this can increase the complexity and difficulty of programming an implanted device appropriately for a given patient.

One source of this complexity stems from the existence of certain programmable modes and features of multiprogrammable pacemaker systems that are mutually incompatible with others, For example, if two features that function to dynamically adjust the same operating parameter of a pacemaker based on different criteria are activated at the same time, operation of one feature could potentially interfere with the operation of the other, and vice versa. One feature may, under certain circumstances be attempting to adjust an operating parameter upwards, while the other one, under the same circumstances, is attempting to adjust that parameter downwards. In that case the intended benefits of both features would potentially not be realized.

As a result of the potential for such conflicts, one solution shown in the prior art has been to make it impossible for the programming clinician to activate mutually conflicting features or to program the implant into mutually-exclusive modes. This has been accomplished in many cases through the use of "programmer interlocks," i.e., safeguards written into the software controlling operation of the programming unit itself that prevent the programmer from issuing impermissible combinations of programming commands to a given implant. Thus, for example, if two selectively activatable features of a pacemaker are deemed by the designer or manufacturer of the pacemaker system to be incompatible, safeguards in the programming unit's software would render the programming unit incapable of activating both of these features in the same implant.

One potential disadvantage of the "programmer interlock" approach to avoiding the selection of incompatible modes or features of an implant is that it limits the clinician's discretion to program an implanted device as he or she deems appropriate for a particular patient. Sometimes incompatible features may only need to run occasionally, so the interlock can prevent a clinician from programming in a potentially therapeutic combination. Another potential disadvantage of this approach is that it can increase the complexity and difficulty of programming for the clinician, and leave a potential source of clinician error in place.

SUMMARY OF THE INVENTION

In view of the foregoing, the present invention is directed to a method and apparatus for permitting simultaneous operation of multiple pacing features in a cardiac pacemaker system.

In accordance with one aspect of the invention, two or more pacing features which operate to cause the dynamic adjustment of a common operational parameter of a pacing system are activatable at the same time. In one embodiment, a prioritization among multiple pacing features is established, such that when two (or more) features which operate to cause adjustment of a common operational parameter, a lower-priority feature will not override an adjustment made by any higher-priority feature. In accordance with another aspect, program feature interlocks may operate to prevent two therapy features from acting on the same parameters at the same time even if they both have the same priority level. In such instances the invention automatically decides which one to use based on physician input or historical device experience data gathered by interaction with the patient.

BRIEF DESCRIPTION OF THE DRAWINGS

The foregoing and other aspects of the present invention may perhaps be best appreciated with reference to a detailed description of a specific embodiment of the invention, when read in conjunction with the accompanying drawings, wherein:

FIGS. 4a and 4b are heuristic flow charts.

FIGS. 5a, and 5 are flow charts representing implementation of pacemaker features using this invention.

DETAILED DESCRIPTION OF A SPECIFIC EMBODIMENT OF THE INVENTION

Figure 1:
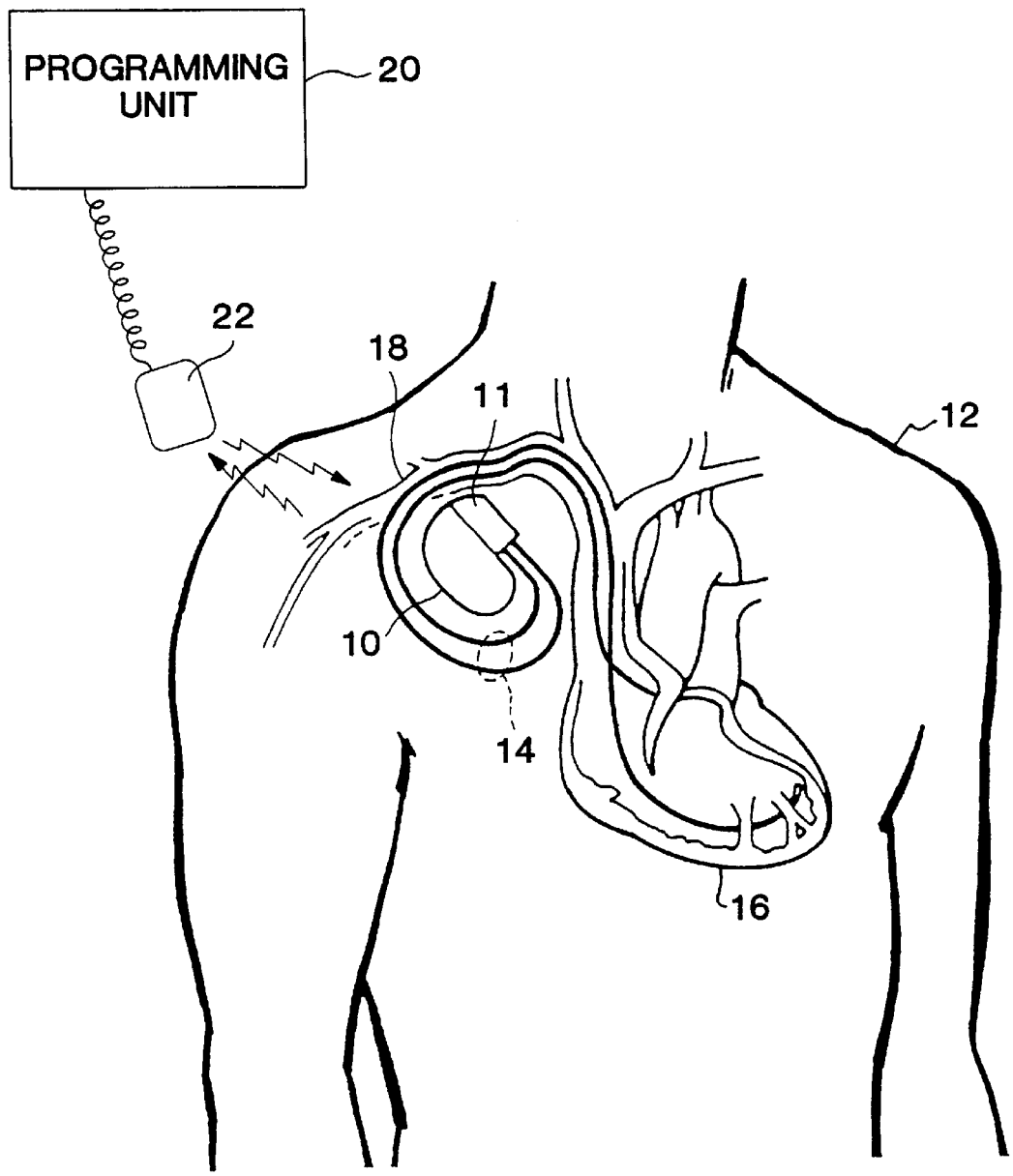
FIG. 1 illustrates an implantable pulse generator system in accordance with one embodiment of the invention.

Referring to FIG. 1, there is shown an illustration of an implantable medical device system in accordance with one embodiment of the invention. The medical device system shown in FIG. 1 includes an implantable device 10—a pacemaker in this embodiment—which has been implanted in a patient 12. In accordance with conventional practice in the art, pacemaker 10 is housed within a hermetically sealed, biologically inert outer canister, which may itself be conductive so as to serve as an indifferent electrode in the pacemaker's pacing/sensing circuit. One or more pacemaker leads, collectively identified with reference numeral 14 in FIG. 1, are electrically coupled to pacemaker 10 in a conventional manner, and extend into the patient's heart 16 via a vein 18. Disposed generally near the distal end of lead(s) 14 are one or more exposed conductive electrodes for receiving electrical cardiac signals and/or for delivering electrical pacing stimuli to heart 16. As will be appreciated by those of ordinary skill in the art, lead(s) 14 may be implanted with its distal end situated in either the atrium or ventricle of heart 16.

Although the present invention will be described herein in one embodiment which includes a pacemaker, those of ordinary skill in the art having the benefit of the present disclosure will appreciate that the present invention may be advantageously practiced in connection with numerous other types of implantable medical device systems.

Also depicted in FIG. 1 is an external programming unit 20 for noninvasive communication with implanted device 10 via uplink and downlink communication channels, in accordance with conventional practice in the art. Associated with programming unit 20 is a programming head 22, for facilitating telemetric communication between implanted device 10 and programmer 20. In many known implantable device systems, a programming head such as that depicted in FIG. 1 is positioned on the patient's body over the implant site of the device, such that one or more antennas within the head can send RF signals to, and receive RF signals from, an antenna disposed within the hermetic enclosure of the implanted device.

Figure 2:
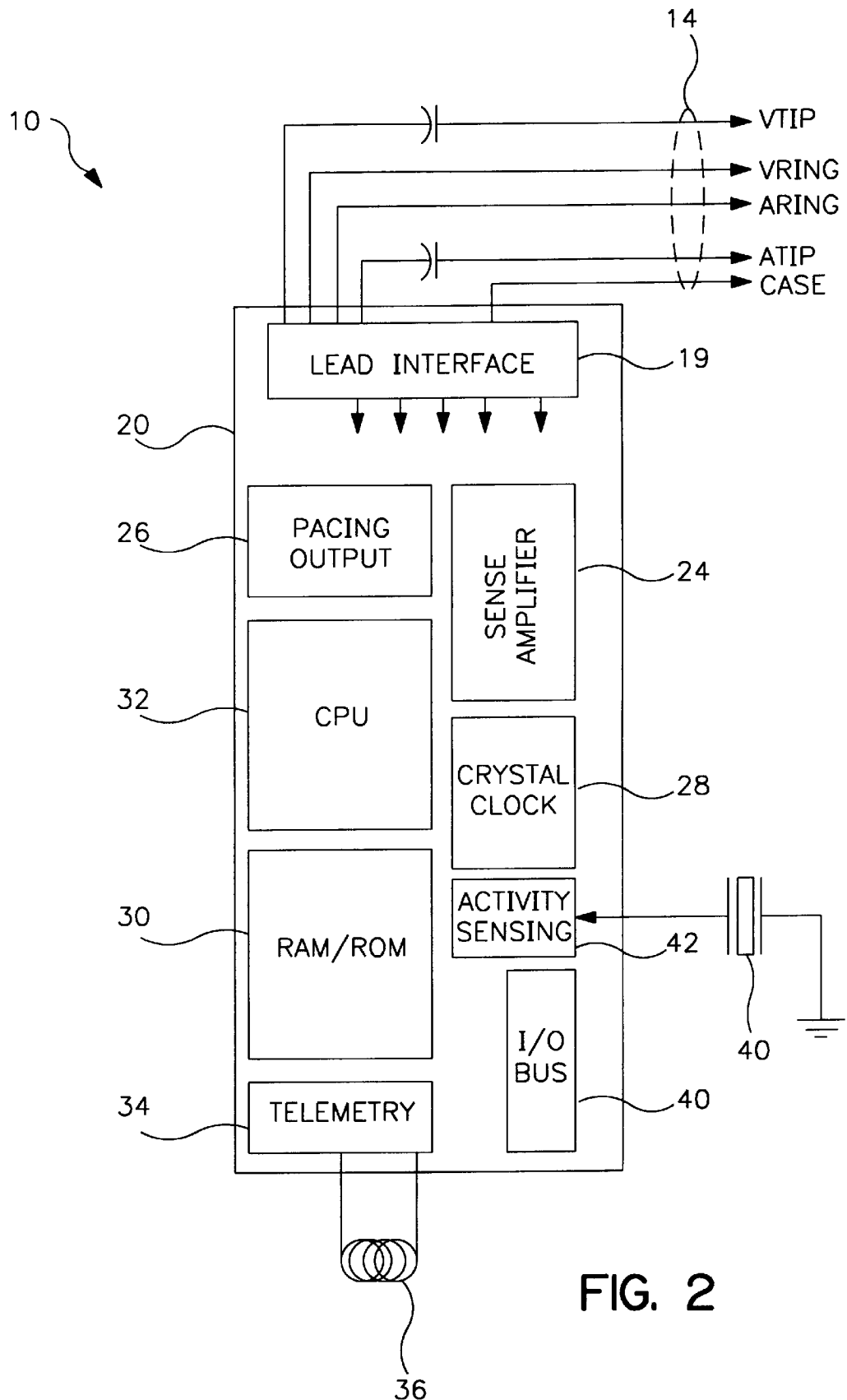
FIG. 2 is simplified functional block diagram of the implantable pulse generator from FIG. 1.

Turning now to FIG. 2, there is shown a block diagram of the electronic circuitry which makes up pulse generator 10 in accordance with the presently disclosed embodiment of the invention. As can be seen from FIG. 2, pacemaker 10 comprises a primary stimulation control circuit 20 for controlling the device's pacing functions. The circuitry associated with stimulation control 20 may be of conventional design, in accordance, for example, with the disclosure of U.S. Pat. No. 5,052,388 to Sivula et al., entitled "Method and Apparatus for Implementing Activity Sensing in a Pulse Generator," or of U.S. Pat. No. 5,271,395 to Wahstrand et al entitled "Method and Apparatus for Rate-Responsive Cardiac Pacing." The Sivula et al. '388 and et al. '395 patents are each hereby incorporated by reference herein in their respective entireties.

To the extent that certain components of pulse generator 10 are conventional in their design and operation, such components will not be described herein in detail, as it is believed that design and implementation of such components would be a matter of routine to those of ordinary skill in the art. For example, stimulation control circuit 20 in FIG. 2 includes sense amplifier circuitry 24, stimulating pulse output circuitry 26, a crystal clock 28, a random-access memory and read-only memory (RAM/ROM) unit 30, a central processing unit (CPU) 32, and an internal communication (telemetry) circuit 34 for facilitating communication with external programmer/control unit 20; all of these components are well-known in the art.

It should be noted here that program features use parameters in the implantable device, in a manner that can be described as producing a state machine for a given set of active therapy features. The various parameter signal values are retained in locations within the memory unit 30. The state machine configured by such therapy feature programs execute on the CPU and memory unit circuitry in a manner well known in many electronic art fields as in this one. Methods for storing electronic equivalents of tables for of such data are exceedingly well known, as are programs for modifying a table holding parameters to one holding other values or even other parameters. Because such programs and the hardware to run them are so conventional and well known further detailed description of them will not be produced here. The specific flow of the programs is described in detail in the text below with reference to the Figures.

With continued reference to FIG. 2, pulse generator 10 is coupled to one or more leads 14 which, when implanted, extend transvenously between the implant site of pulse generator 10 and the patient's heart 16, as previously noted with reference to FIG. 1. Physically, the connections between leads 14 and the various internal components of pulse generator 10 are facilitated by means of a conventional connector block assembly 11, shown in FIG. 1 but not shown in FIG. 2. Electrically, the coupling of the conductors of leads and internal electrical components of pulse generator 10 is facilitated by means of a lead interface circuit 19 which functions, in a multiplexer-like manner, to selectively and dynamically establish necessary connections between various conductors in leads 14, including for example, atrial tip and ring electrode conductors ATP and ARING and ventricular tip and ring electrode conductors VTIP and VRING, and individual electrical components of pulse generator 10, as would be familiar to those of ordinary skill in the art. For the sake of clarity, the specific connections between leads 14 and the various components of pulse generator 10 are shown in FIG. 2, although it will be clear to those of ordinary skill in the art that, for example, leads 14 will necessarily be coupled, either directly or indirectly, to sense amplifier circuitry 24 and stimulating pulse output circuit 26, in accordance with common practice, such that cardiac electrical signals may be conveyed to sensing circuitry 24, and such that stimulating pulses may be delivered to cardiac tissue, via leads 14.

As previously noted, stimulation control circuit 20 includes central processing unit 32 which may be an off-the-shelf programnmable microprocessor or microcontroller, but in the presently preferred embodiment of the invention is a custom integrated circuit. (Those of ordinary skill in the art will appreciate that still another alternative would be for pacemaker 10 to be controlled not by a processor, but by means of custom circuitry implementing a state-machine type of operational control. It is believed that persons of ordinary skill in the art having the benefit of the present disclosure would be able to readily adapt the presently disclosed embodiment to a state-machine based system.)

Although specific connections between CPU 32 and other components of stimulation control circuit 20 are not shown in FIG. 2, it will be apparent to those of ordinary skill in the art that CPU 32 functions to control the timed operation of stimulating pulse output circuit 26 and sense amplifier circuit 24 under control of programming stored in RAM/ROM unit 30, and using input signals from sense amplifier circuitry 24 and activity sensing circuitry 42. It is believed that those of ordinary skill in the art will be familiar with such an operative arrangement.

With continued reference to FIG. 2, crystal oscillator circuit 28, in he presently preferred embodiment a 32,768-Hz crystal controlled oscillator, provides main timing clock signals to stimulation control circuit 20. Again, the lines over which such clocking signals are provided to the various timed components of pulse generator 10 (e.g., microprocessor 32) are omitted from FIG. 2 for the sake of clarity.

It is to be understood that the various components of pulse generator 10 depicted in FIG. 2 are powered by means of a battery (not shown) which is contained within the hermetic enclosure of pacemaker 10, in accordance with common practice in the art, although numerous other power sources are currently known and could be easily substituted for battery power as they become more technically advanced, but for now we prefer battery powered devices. For the sake of clarity in the Figures, the battery and the connections between it and the other components of pulse generator 10 are not shown.

Stimulating pulse output circuit 26, which functions to generate cardiac stimuli under control of pacing trigger signals issued by CPU 32, may be, for example, of the type disclosed in U.S. Pat. No. 4,476,868 to Thompson, entitled "Body Stimulator Output Circuit," which patent is hereby incorporated by reference herein in its entirety. Again, however, it is believed that those of ordinary skill in the art could select from among many various types of prior art pacing output circuits which would be suitable for the purposes of practicing the present invention.

Sense amplifier circuit 24, which is of conventional design, functions to receive electrical cardiac signals from leads 14 and process such signals to derive event signals from leads 14 and to process such signals to derive event signals reflecting the occurrence of specific cardiac electrical events, including atrial contractions (P-waves) and ventricular contractions (R-waves). These event-indicating signals are provided to CPU 32 for use by CPU in controlling the synchronous stinulating operations of pulse generator 10 in accordance with common practice in the art. In addition, these event indicating signals may be communicated, via uplink transmission, to external programming unit 20 for visual display to a physician or clinician.

Finally, FIG. 2 shows that pacemaker 10 includes an activity sensor 40, coupled to activity sensing circuitry 42. Sensor 40, which in the presently disclosed embodiment of the invention is a piezoelectric transducer or the like, provides an electrical signal to activity sensing circuitry 42 reflecting the level of the pacemaker patient's activity level. Activity sensing circuit processes the activity signal and provides it (or a quantification of it) to CPU 32, such that the patient's activity level may be among those factors relied upon the pacemaker 10 in operating in accordance with the desired pacing algorithm although the algorithm may look to input from inferences drawn from impedance measurement or the monitored EKG morphology, various other sensors like temperature, oxygen, heart motion, acoustic or other sensors alone or in combination if the designer of the device prefers. A pacemaker which employs a piezoelectric activity sensor and associated circuitry suitable for the purposes of practicing the present invention is described in more detail in U.S. Pat. No. 4,485,813 to Anderson et alhereby incorporated by reference herein in its entirety.

Those of ordinary skill in the art will appreciate that pacemaker 10 may include numerous other components and subsystems, for example, other types of physiologic sensors and associated circuitry, backup or redundant control of physiologic sensors and associated circuitry, and so forth. To the extent that such additional components or subsystems are not discussed herein, it is believed that their presence or absence in pacemaker 10 is not relevant or necessary for an understanding of the present invention.

In accordance with conventional pacemaker systems, normal, chronic operation of pacemaker 10 is carried out under control of CPU 32, based primarily upon: (1) control programming stored in RAM/ROM unit 30; (2) programmed operational parameter values, selected by the programming clinician and also stored RAM/ROM unit 30 or on-board CPU registers; (3) input signals from sense amplifier circuitry 24 reflecting the detected occurrence of intrinsic cardiac electrical activity; and (4) input signals from other sensors, such as activity sensing circuitry 42, reflecting certain physiologic conditions of the patient. This, control programming and the algorithm, together determine the pacemaker's behavior given a particular combination of sense amplifier and sensor signals.

In the presently disclosed embodiment of the invention, and in accordance with known pacemaker systems, CPU 32 performs various numeric computations to implement its pacing algorithm. Many such computations are performed on a regular basis, for example, on a cardiac cycle basis. For example, to implement its rate-responsive functionality, CPU 32 makes regular calculations, based upon activity sensor inputs, to determine on a dynamic, cycle-to-cycle basis, the appropriate base pacing rate for the patient. Various operational parameters, for example, the A-V interval following an atrial pace and following an atrial sense, are adjusted on a cycle-to-cycle basis. Again, it is believed that such an operational arrangement will be well-known to those of ordinary skill in the art.

An example of a pacemaker which computes or adjusts various operational parameter values on a cycle-to-cycle basis is described in some detail in U.S. Pat. No. 5,271,395 to Wahlstrand et al., entitled "Method and Apparatus for Rate-Responsive Cardiac Pacing," which patent is hereby incorporated by reference herein in its entirety. In the device described in the Wahlstrand et al. '395 patent, various operational parameters are adjusted during what can be referred to as a parameter adjustment cycle that occurs after each ventricular event (pace or sense). These dynamically adjusted parameter values are then used to control the timing of events during the next cardiac cycle.

The control programming for pacemaker 10 stored in RAM/ROM unit 30 preferably includes programming for implementing a plurality of pacing therapy features that cause certain operational parameters of pacemaker 10 to be adjusted on a dynamic basis, for example, on a cycle-to-cycle basis. Implementation of these various features thus also involves computation of various quantities.

The various pacing therapy features provided for by the pacemaker's control programming are preferably selectively activatable and deactivatable features which may or may not be appropriate for any given patient. In some cases, two different features may be intended to dynamically adjust the same operational parameter of pacemaker 10. However, two such features may adjust the common operational parameter for different reasons, in different ways, and based on differing adjustment criteria. For the purposes of the present disclosure, any two such features will be said to be "mutually exclusive" with respect to one another. For example, one such common parameter of significance is the Ventricular Escape Interval or Atrial to Ventricular Escape Interval, which would be used by many different therapies involving the pacemaker.

In the presently preferred embodiment of the invention, pacemaker 10 has several pacing therapy features that, when activated, cause certain operational parameter values to be periodically adjusted. In most cases, as will be hereinafter described in further detail, such adjustment occurs once per cardiac cycle, and in particular, during 'parameter adjustment windows/or time frames that occur following every ventricular pace and ventricular sense event, but some occur at periodicity's determined by a program that accommodates their propose and power consumption requirements, for example, or periodicity timing can be timed to be tied to occur at other periods for other known reasons based on a single triggering event or a pacemaker monitored histogram of triggering events. Using these or other data stored in histograms located in memory and filled as the data becomes manifest provides for additional levels of automatic control over device functioning as described below.

The following summarizes the various pacing therapy features of interest for the purpose of the present disclosure; VENTRICULAR AUTOCAPTURE (ALSO KNOWN AS CAPTURE MANAGEMENT)

This feature, available in DDDR, DDD, DDIR, DDI, VDD, VVIR, and VVI modes, when activated, functions to measure the voltage and pulse width necessary for pacing pulse efficacy, called the pacing threshold. This is a desirable feature of pacemakers(but as yet it is not common to find pacemakers with automatic ambulatory capture measurement functions). The feature adjusts the Escape Interval, the Sense-AV, Paced-AV intervals and the post-ventricular atrial refractory periods to accomplish its task.

PREMATURE VENTRICULAR CONTRACTION (PVC) RESPONSE

This feature, available in DDDR, DDD, DDIR, DDI, and VDD modes, functions to adjust the post-ventricular atrial refractory period (PVARP) parameter if a premature ventricular contraction (PVC) is detected, where a PVC is defined as two ventricular occurring without an intervening atrial event. This feature (or extension) prevents retrograde atrial activity from initiating a pacemaker mediated tachycardia.

PACEMAKER-MEDIATED TACHYCARDIA (PMT) INTERVENTION

This feature, available in DDDR, DDD and VDD modes, functions to adjust PVARP in the event that predefined pacemaker-mediated tachycardia (PMT) criteria are satisfied. In the presently disclosed embodiment of the invention, the PMT criteria are fulfilled if a predetermined number (e.g., eight) ventricular pace-atrial sense (VP-AS0 sequences in a row are detected, where the length of each VP-AS sequences is below a predetermined value. If the criteria are fulfilled, PVARP is then extended by a predetermined amount, e.g., 400-mSec for one cycle to break the PMT. An example of this therapy feature is U.S. Pat. No. 5,312,450 (Markowitz) (as with other patent references incorporated herein by reference in its entirety).

MODE SWITCHING

This feature, which makes some variable values change in response to atrial tachycardia or rhythm disturbances is available in DDDR, DDD and VDD modes. Generally this feature makes transient adjustments to improve Atrial Arrthymia detection and Mode switching. Mode switching can affect or adjust the Escape Interval and PVARP parameters, the V-A Interval parameter, the A-V interval following an atrial sense (known as the SAV parameter), and the A-V interval following and atrial pace (known as the AV parameter), if an atrial tachycardia or arrhythmia is detected. In addition, this feature switches the pacing mode from DDDR to DDIR, or from DDD to DDI, or from VDD to VVI, in response the atrial arrhythmia. These adjustments are intended to prevent the pacemaker from tracking the atrial arrhythmia.

RATE DROP RESPONSE

This feature, available in DDD and DDI modes, defines the pacemaker's response to precipitous drop in intrinsic cardiac rate, which can occur, for example, in patients with vasal-vagal syncope. If a precipitous drop in intrinsic rate is detected, this feature can cause the Escape Interval parameter to be temporarily decreased, resulting in a high pacing rate, in order to increase cardiac output and reduce the likelihood of the patient passingout due to a Vasovogal Syncopal episode and may also impose restrictions further changes in the rate following such an episode.

This feature, available in DDDR mode, is provided to take full advantage of any intrinsic cardiac activity the patient has.

When activated, this feature causes the Escape Interval to be periodically increased above its normally programmed value (resulting in a slower pacing rate), to determine whether intrinsic cardiac activity is being masked out as a result of an unnecessarily fast programmed rate.

RATE-ADAPTIVE A-V DELAY

This feature, available in DDDR, DDD, DDIR, DVIR, DOOR, and VDD modes, causes a shortening of the A-V delay (the SAV parameter) in response to faster intrinsic atrial rates, and causes a shortening in the pace related A-V parameter (PAV) in response to faster paced atrial rates. This is believed to more accurately mimic natural physiologic response.

ADAPTIVE A-V DELAY

This feature, available in DDDR, DDD, DDIR, and VDD modes, periodically adjust the programmed A-V delay parameters (SAV and PAV) if sensing information suggests that A-V conduction is occurring but at a conduction interval that is slow in comparison to the programmed A-V delay, such that unnecessary ventricular paces are delivered. In particular, the Adaptive A-V Delay feature makes additions or subtractions to the SAV and PAV parameters based on measured A-V conduction times. For a predetermined number of beats (e.g., 16), the pacemaker measures the A-V conduction time and classifies ventricular senses based on these measured conduction times as either "too short" of "too long."

A-V HYSTERESIS

This feature, available in DDDR, DDD, DDIR, and VDD modes, like the Adaptive A-V Delay feature described above, functions to adjust the SAV and PAV parameters, if sensory input suggests that A-V conduction is being masked out as a result of an inappropriately short programmed A-V delay. A-V Hysteresis differs from Adaptive A-V Delay in that the A-V Hysteresis features simply adds a programmed increment to the SAV and Pav parameters when a ventricular sense occurs.

HYPERTROPIC OBSTRUCTIVE CARDIOMYOPATHY A-V RESPONSE

This feature, available in DDDR and DDD modes, functions to adjust the programmed PAV and SAV parameters in patients exhibiting symptoms of hypertropic obstructive cardiomyopathy (HOCM). In particular, the HOCM A-V Response feature attempts to always maintain ventricular capture at the longest A-V delay possible (without lapsing into fusion or pseudo-fusion). Other HOCM algorithms may also determine the AV delay to assure optimal hemodynamic performance. Some forms of HOCM therapy even allow for non-sinus tracking operation. All such HOCM palliative responses are used to enhance cardiac output in HOCM patients.

ATRIAL BASED TIMING (Adjusting the A—A interval)

The Atrial Based Timing is used to maintain proper atrial pacing intervals which could otherwise become unstable in view of the various adjustments to other parameters (PAV, SAV, Escape Interval, etc . . . ) made in accordance with other therapy or therapy extension features as discussed above. The A—A Timing feature can be summarized as follows: If the last A-V interval is shorter than the next A-V interval, the V-A interval is extended by the difference between them, in order to maintain the appropriate A—A timing.

SENSOR-VARIED PVARP

This feature, available in DDDR, DDD, DDIR, and VDD modes, adjust PVARP as a function of activity sensing by rate response sensing circuitry 42.

AUTO PVARP

This feature, available in DDDR, DDD, and VDD modes, functions to adjust PVARP and SAV in order to prevent inappropriate 2:1 block, a situation in which the length of PVARP causes the pacemaker to track only every other atrial beat. In accordance with this feature, an appropriate 2:1 block point is periodically calculated based on the current atrial rate. In the presently preferred embodiment of the invention, this point id defined as 30 BPM above the mean atrial rate. PVARP is then adjusted based on the current A-V delay to produce a total atrial refractory period (TARP) equal to the desired 2:1 block target. If achieving this 2:1 block point would result in a PVARP that is below a programmed minimum PVARP value, the A-V delay parameter(s) are shortened.

As noted above, the present invention is concerned with permitting certain of the above-described features, which may operate to adjust common operational parameters of the pacemaker in different ways and based on different criteria, to be activated at once, whereas in the prior art such "mutually exclusive" features are typically not permitted to be simultaneously activated.

Notwithstanding this objective of the present invention, there nonetheless remain certain features that are mutually exclusive to such a degree that they cannot be simultaneously active. For these features, a programmer interlock is preferably implemented, such that simultaneous activation of these features is prohibited by operation of the programming unit.

Example of such mutually exclusive combinations of features in the presently disclosed embodiment of the invention include: Mode Switching and Rate Drop Response; Adaptive A-V Delay. A-V Hysteresis and HOCM A-V Delay; and Sensor-Varied PVARP and Auto PVARP.

Notwithstanding the need for programmer interlocks in connection with these certain combinations of features, there are other combinations of features that, in accordance with the present invention can be permitted to be simultaneously active even though they operate to adjust a common operational parameter.

For example, the Mode Switching and Sinus Preference features both operate to adjust the Escape Interval parameter; the Mode Switching and AA Timing features both operate to adjust the V-A Interval parameter; the Mode Switching, Rate-Adaptive A-V Delay, and HOCM A-V Delay features each operate to adjust the SAV and PAV parameters; and the PMT Intervention, Mode Switching, and Sensor Varied PVARP (or Automatic PVARP) features all operate to adjust the PVARP parameter.

While each of these combinations would typically, in the prior art be regarded as mutually-exclusive and hence subjected programmer interlocked, it is a an a feature of the present invention that these combinations be permitted to be simultaneously active.

Also, where other therapeutic features may be available, the principles of this invention can be extended to cover these therapies or modes as well if managed as described in the general case described with reference to FIGS. 4a–c below.

To accomplish this objective in accordance with the present invention and using only those therapies and modes delineated above, the various features are assigned relative priorities with respect to one another. the following Table 2 summarizes the priority assignment in accordance with the presently disclosed embodiment of the invention.

TABLE 2

| FEATURE/ PROGRAM | Operational Escape Interval | Parameter V-A Interval | SAV | PAV | PVARP |
|---|---|---|---|---|---|
| Ventricular Threshold Tracking | 1 | | 1 | 1 | 1 |
| PMT Intervention | | | | | 2 |
| Mode Switching | 2 | 1 | 2 | 2 | 3 |
| Rate Drop Response | 2 | | | | |
| Sinus Preference | 3 | | | | |
| Rate Adaptive A-V Delay | | | 5 | 3 | |
| A-V Hysteresis | | | 4 | 4 | |
| HOCM A-V Delay | | | 4 | 4 | |
| Sensor Varied PVARP | | | | | 4 |
| Automatic PVARP | | | 3 | | 4 |
| A-A Timing | | 2 | | | |
| Rate Response | 4 | | | | |
| PVC Response | | | | | 2 |

In Table 2, the numbers 1–4 represent the relative priority of the various features with respect to one another in relation to modifying a given operational parameter (1 is highest priority, 4 is lowest). In each column of Table 2, if two features have the same priority, this reflects the situation, discussed above, where a programmer interlock preventing simultaneous activation of those features, is still necessary (or in the case of PMT intervention and PVC response, the definition of conditions monitored by these features makes their occurrence at the same time impossible).

Figure 3A:
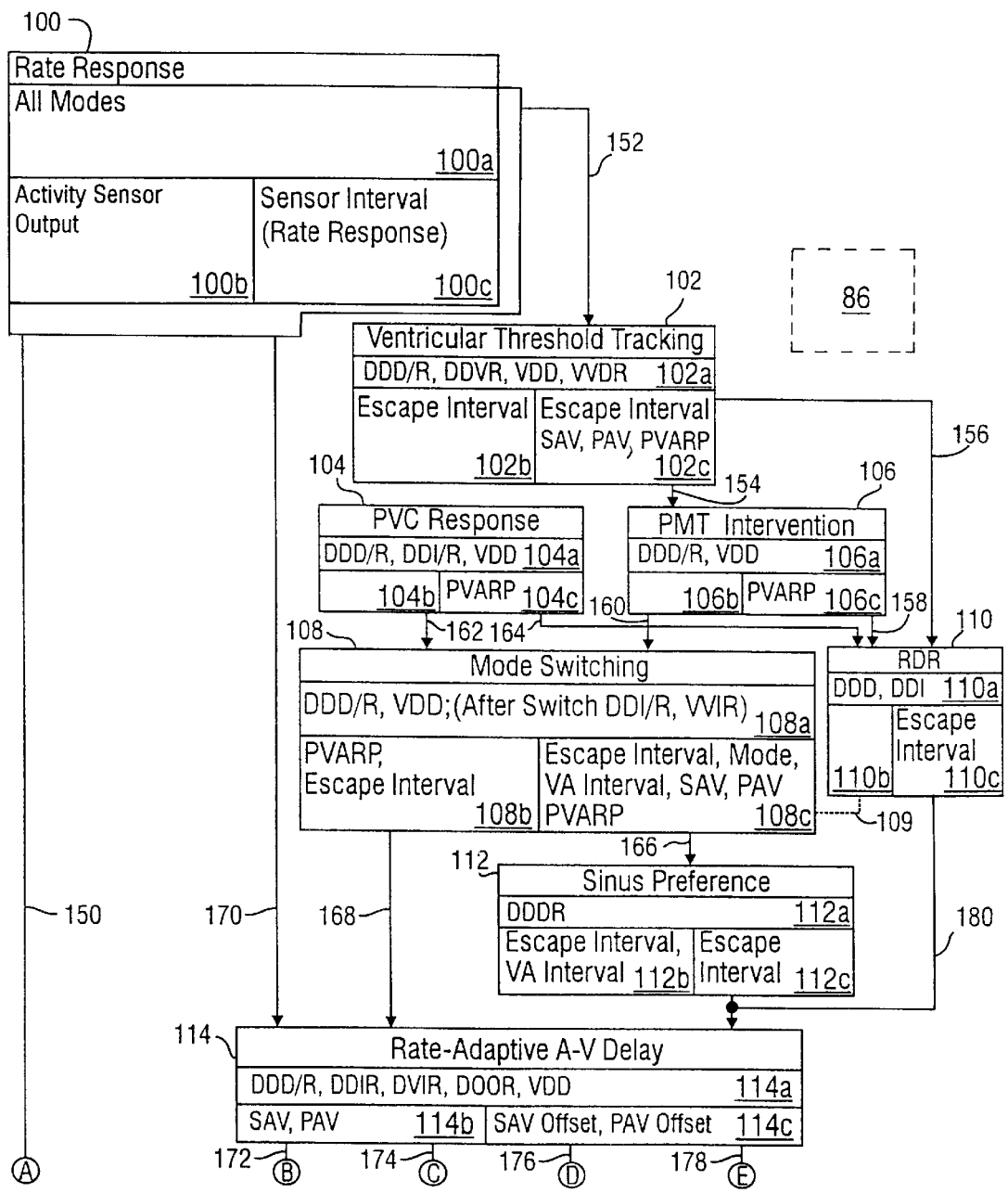
FIGS. 3a and 3b combine to form a flow diagram illustrating the operation of the pulse generator from FIG. 1.
Figure 3B:
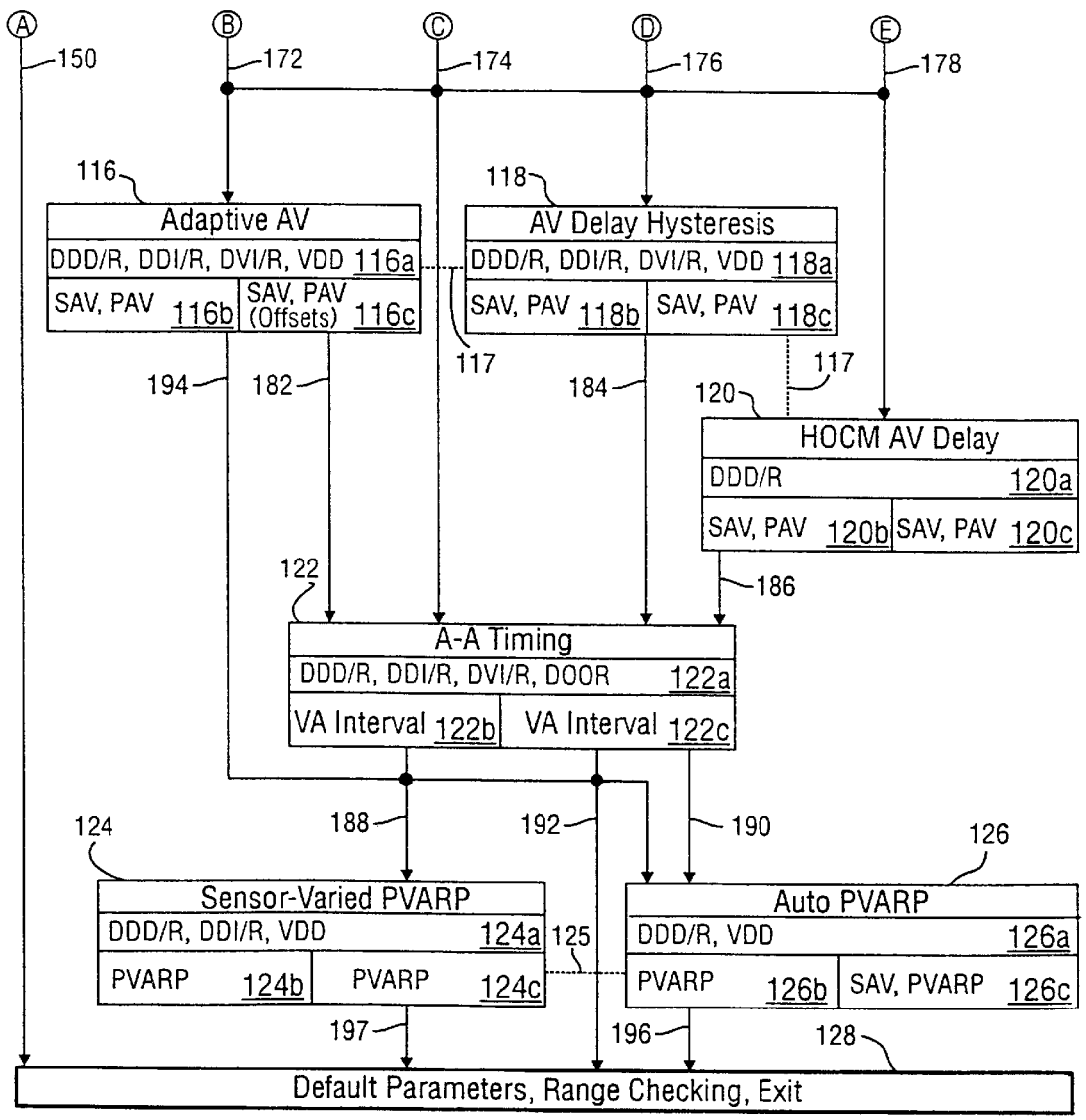

The manner in which the relative priorities set forth in Table 2 are implemented by pacemaker 10 in accordance with the presently disclosed embodiment of the invention can perhaps be best appreciated with reference to the flow diagram of FIGS. 3a and 3b. It must be emphasized that if programming is done using this invention, the programmer would reset the table to modify priorities for particular patients, and this would modify the flow chart.

Block 100 in FIG. 3a indicates that pulse generator 10 in accordance with the presently disclosed embodiment of the invention has a Rate Response feature which, as described above, functions to adjust the pacing rate in accordance with metabolic demand (i.e., activity level). Sub-block 100a indicates that the Rate Responsive feature (when activated) is available in all modes. sub-block 100b indicates that the Rate response feature takes the output of activity sensor circuit 42 as an input. Sub-block 100c indicates that the Rate Response feature adjusts the Sensor Interval parameter. Unlike most of the remaining features of pacemaker 10, the Rate Response feature operates essentially independently from others, and is not synchronized with respect to cardiac pacing cycles.

(The convention of block 100 is used for each block in FIGS. 3a and 3b. In particular, each block represents one pacing feature or mode of the device; each sub-block 100a, 102a, 104a, etc . . . indicates the pacing modes in which the feature is available; each sub-block 100b, 102b, 104b, etc . . . indicates the parameter value used as an input for the feature; and each sub-block 100c, 102c, 104c, ect. . . . indicates the parameter or parameters adjusted by the feature.)

If none of the programmably activatable features of pulse generator 10 other than the Rate Responsive feature are activated, once the Sensor Interval is computed in block 100, default parameter values are used, subject to checks for out-of-range violations and the like, as reflected by transition 150 from block 100 to block 128.

If the Ventricular Threshold Tracking feature is activated, on the other hand, transition 152 from block 100 to block 102 is taken. Block 102 indicates that the ventricular Threshold Tracking feature is available in DDD, DDDR, DDVR, VDD, and VVDR modes (sub-block 102a), and uses ? Escape Interval, SAV and PAV parameter values.

Next, if the PVC Intervention feature is activated, transition 154 is taken to block 106. The PVC Intervention feature, available in DDD, DDDR, and VDD modes (sub-block 106a), computes a new PVARP parameter value (sub-block 106c) if PVC detection criteria are fulfilled, as described above.

If the PVC Intervention feature is not activated, transition 156 is taken from block 102 to 110. (If PVC Intervention is activated, transition 158 is taken from block 106 to 110). Block 110 corresponds to the Rate Drop Response (RDR) feature, available in DDD and DDI modes (sub-block 110a). The RDR feature computes a new Escape Interval parameter value (sub-block 110c) if the criteria defining a precipitous rate drop are fulfilled, as described above.

As noted above, the Mode Switching and Rate Drop Response features are deemed to be mutually exclusive, so that a programmer inter lock is put in place to prohibit simultaneous activation of these features; this is by dashed line 109 in FIG. 3a. If the Rate Drop Response feature is activated, transition 158 is taken from block 106 to block 110, as just described. If the Rate Drop Response feature is activated, transition 158 is taken from block 106 to block 110, as just described. If instead the Mode Switching feature is activated, transition 160 from block 106 to block 108 is taken.

The Mode Switching feature is available in DDD, DDDR, and VDD modes and, if a mode switch is made, leaves pulse generator 10 in DDI, DDIR, or VVIR modes (sub-block 108a). The Mode Switching feature checks the current PVARP and Escape Interval parameter values (sub-block 108b), and is capable of adjusting the Escape Interval, Pacing Mode, VA Interval, SAV, PAV and PVARP parameter values(sub-block 108c), as described above.

Pulse generator 10 also has a Premature Ventricular Contraction (PVC) Response feature, described above. If a PVC is detected, entry into the flow diagram of FIGS. 3a and 3b is to PVC Response block 104. The PVC Response is available in DDD, DDDR, DDI, DDIR, and VDD modes (sub-block 104a) and, if PVC detection criteria are fulfilled, functions to adjust PVARP (sub-block 104c). Then, depending upon whether the Mode Switching feature or the Rate Drop Response feature is activated, transition 162 or 164 is taken to block 108 or 110, respectively.

If the Sinus Preference feature is activated, transition 166 is taken from block 108 to block 112. In DDDR mode (sub-block 112a), the Sinus Preference feature checks the current Escape Interval and VA Interval parameter values (sub-block 112b), and periodically lengthens the Escape Interval values (sub-block 112c).

If the Sinus Preference feature is not activated, transition 168 is taken from block 108 to Rate Adaptive A-V Delay block 114. The Rate-Adaptive A-V Delay feature is available in DDD, DDDR, DDIR, DOOR, and VDD modes (sub-block 114a), and based on the current SAV and PAV parameter values (sub-block 114b) computes SAV Offset and PAV Offset parameter values to shorten the A-V delay in response to faster intrinsic atrial rates. In the embodiment of the invention, this computation of offset parameter values does not prevent subsequent adjustment of SAV and PAV by other features.

If none of the features associated with blocks 102–112 in FIG. 3a are activated, transition 170 is taken from block 100 directly to block 114.

(It is to be understood that the labels "A" through "F" at the bottom of FIG. 3a serve to indicate how transitions 150, 172, 174, 176, 178, and 180 continue from FIG. 3a to FIG. 3b.)

As previously noted, the Adaptive A-V Delay Hysteresis, and HOCM A-V Delay features are mutually exclusive and hence programmer interlocked. This is reflected by dashed line 117 in FIG. 3b. Thus, from Rate Adaptive A-V Delay block 114 in FIG. 3a, there are four possible transitions, depending upon which one of these features, if any, is activated; transition 172, if the Adaptive A-V Delay feature is activated; transition 176 if the A-V Hysteresis feature is activated; transition 178 if the HOCM A-V Delay feature is activated; or transition 174 if none of these three features is activated.

If the Adaptive A-V Delay feature is activated, in DDD, DDDR, DDI, DDIR, DVI, DVIR, and VDD modes (sub-block 116a), then the SAV and PAV parameter values are checked (sub-block 116b) and sometimes adjusted (sub-block 116c) in accordance with that feature. Likewise, the SAV and PAV parameters are checked and sometimes changed in accordance with either the A-V Delay Hysteresis or HOCM A-V Delay features are activated. In any of these cases, next a transition (182, 184, 186) can be taken to A—A Timing block 122. Transition 174 from block 114 to block 122 is made if none of the mutually exclusive A-V delay features is activated.

The A—A Timing feature is available in DDD, DDDR, DDI, DDIR, DVI, DVIR, and DOOR modes (sub-block 122a), and as described above checks (sub-block 122b) and may adjust (sub-block 122c) the V-A Interval parameter value.

As noted above, the Sensor-Varied PVARP and Auto PVARP features are mutually exclusive, as reflected by dashed line 125 in FIG. 3b. Thus, from A—A Timing block 122, transitions can be made either to Sensor-Varied PVARP block 124 (transition 188), to Auto PVARP block 124 or 126.

The Sensor-varied PVARP feature, available in DDD, DDDR, DDI, DDIR, and VDD modes (sub-block 124b)and may adjust (sub-block 124c) the PVARP parameter value based on the output of activity sensor circuitry 42. The Auto PVARP feature, available in DDD, DDDR, and VDD modes (sub-block 126a), checks the PVARP parameter value (sub-block 126b) and may adjust the SAV and PVARP parameters (sub-block 126c) as discussed above.

From Sensor-Varied PVARP block 124, transition 194 is taken to Default Parameters block 128; from Auto PVARP block 126, transition 196 is taken to Default Parameters block 128. Default Parameters block 128 represents the stage at which default parameter values are assigned to all parameters not set or adjusted in accordance with one or more of the programmable features described with reference to FIGS. 3a and 3b. This concludes the parameter-setting process in accordance with the presently disclosed embodiment of the invention.

Those of ordinary skill in the art will appreciate that the parameter-setting process described above with reference to FIGS. 3a and 3b may be conducted by control circuitry 20 executing control programming stored within RAM/ROM unit 30. Accordingly, the scheme of relative priority of the various selectively activatable features is embodied in the invention, may itself be adjusted or altered, either automatically (for example, in response to diagnostic data collected by pacemaker 10 which indicate that a given pacing feature is no longer appropriate for the patient) or manually, i.e., by a physician or clinician using programming unit 20. This flexibility would enable the physician to determine, on a patient-by-patient basis, the relative importance and priority of the various pacing features available.

For example PMT intervention is enabled by default to a high priority. If subsequent activation of PMT are detected to be inappropriately triggering on sinus tachycardia, the device may de-emphasize the priority of PMT intervention to improve sensitivity of mode switching (which also affects PVARP). This could be done for example by monitoring sinus rate after PMT intervention to detect a change in atrial rate (a decrease) consistent with PMT termination. No change in sinus rate would suggest the rhythm is not PMT. The device could store the results in a histogram in memory and periodically review results to evaluate this current priority scheme. (It should be noted that memory stored histogram data can take many forms; conters, flags, trend indicated, tables, lists of variables and so forth can be used. These can be applied to help direct automatic switching between rates of therapy delivery, their respective priorities, or even their abandonment in favor of a gfall back therapy.)

From the foregoing detailed description of a specific embodiment of the invention, it should be apparent that a method and apparatus for the simultaneous administration of multiple cardiac pacing therapies has been disclosed. In accordance with one aspect of the invention, pacing therapies which in some cases operate to adjust a common parameter and hence maybe regarded as mutually exclusive are nonetheless capable of being simultaneously activated. As mentioned earlier the use of a lockout scheme can be used to avoid this. If the lockout feature is programmed off and the priorities of the two such pacing therapies are set to the same level, the automatic adjustment priority of a program access based on history of feature usage which is described in the last paragraph such as automatic adjustment can be implemented to change priorities in various ways. To illustrate such a feature relative to the diagrams of FIGS. 3a and 3b, a dotted lined box 86 is en related to the lockouts also indicated as dotted lines, 109,117 and 125 as described above. Thus box 86 is a program that can check the relevance of priority level set for a therapy feature program's access to a common parameter. And it also is a program that activates lockouts of therapy feature programs that share a common parameter so that in the alternative it functions without regard to patientt history.

While several selectively activatable diagnostic and therapeutic features have been discussed herein, it is believed that those of ordinary skill in the art having the benefit of the present disclosure would be readily capable of practicing the invention in connection with a pacemaker or other implantable device having more, fewer, and/or different features and operational modes. Programming a lockout feature which can alternatively function as an automatic variable charger based or collected patient/device history data is easily within the skill of this art.

With regard to the establishment of the priority value correspondence to various therapy feature programs organizing the memory so as to contain values representative of priority organization sets for each feature and storing these in some memory circuits. Also a programmer device may contain as default tables like the ones below, corresponding to FIGS. 5a and b which can be downloaded into the implantable device memory a process also well known in the art.

There are many ways to do this change of table operation which would be quite different for each pacemaker/programmer system, so because of this and because this is well within the ordinary skill level in this art no detailed description is made of this.

It is sufficient to mention that currently used modern pacemakers support the capability of new feature downloading through telemetry into RAM and are thus configured to run as if the feature was included in the device when it was first implanted. Accordingly it is advantageous to be able to modify the priority tables to accommodate newly developed therapies and their interlocks. Experimental clinicians may want to develop and test the best priority table to provide it as a default for certain conditions to the practicing physician to ease the physician's burden in checking the valuation of priority for every newly installed therapy delivery program. Or most preferably with each set of therapy feature programs the manufacture will supply a table of default values for all shared parameters. On the other hand, if a Physician desires, this adjustable memory of positive values feature permits variation of priority between patients and even in a single patient as conditions of health vary.

For example, a fully featured pacemaker may have an algorithm to treat a specific disease added via downloading and the flowchart representation of the prioritization of these features and their order of occurrence could look like that in FIG. 4a. [prior to the downloading] and like the flow chart of FIG. 4b after. In this example the downloaded feature is a new automatic PVARP adjustment algorithm. This new algorithm has been given a higher priority for affecting the PVARP parameter than the old Auto PVARP algorithm, but not higher than mode switch.

These two PVARP feature programs could be the "Sensor Varied PVARP' and "Automatic PVARP" referred to in Table 2. Note that their priority is "4" for both programs. The apparent inconsistency is handled by FIG. 4b's flow diagram since the new version is inserted into the diagram prior to activation of the old. In this way if the new PVARP affecting program changes PVARP, it can lock out the ability of the next program in the flow chart with an identical priority value to modify that parameter. The easy way to implement this although there are many would be to establish a counter that recycles for each shared parameter that has two or more Therapy feature programs which can affect that parameter: and for any two programs to be interlocked, count to 1 for the priority program (having the same priority level) or leave the counter at 0 for no change during this pass through of the feature set of all therapy feature programs. Thus if New PVARP had changed PVARP's value on this run-through, Old PVARP could not. Additionally some interlocked programs cannot operate on the same parameter at the same cycle because it is not possible to run one when the other is run. For example, a vasovagal syncope, (VVS) monitor program above called the Rate Drop Response algorithm (RDR) cannot run after a mode switch since after a mode switch the pacemaker is sensing an atrial arrhythmia so it cannot tracking an atrial (sinus) rate; and the RDR program needs an atrial rate to operate.

To understand how the flow chart is modified consider that the flow of operational or therapy features would be organized by the closest patch point in the code following the program the particular new operation is to follow, linking the new program's end point to the program that used to be pointed to before the addition of the new feature program. This factory supplied program would also have a default table to replace the Table 2 parameter modification priority to accommodate the new feature if necessary.

Please refer to FIGS. 5a and 5b and the tables 3 and 4 which, respectively, relate to each other. These Figs are simplified to leave out the description's of any but the relevant therapy Peature programs MS(Mode Switch) 502 and 506. and the HOCM (HYPERTROPIC Obstructive CARDIOMYOPATHY) therapy feature 504 and 509. The rest of the features are labeled 503A-E and 507 A-E.

Here we assume a pacemaker with a modeswitching algorithm to change from atrial tracking (following atrial or sinus rate) to non-tracking mode pursuant to the finding of atrial arrhythmia indications. At the same time, a HOCM program may exist designed to achieve pacing in the ventricular for the apex based on an algorithm that changes the size of the AV interval. If the device with such features performs a mode switch to non-tracking mode, the benefit of the HOCM feature will be lost. In some patients, the occurrence of atrial arrhythmia's may be of short duration, but the HOCM feature may be extremely valuable because the patient becomes symptomatic when the HOCM feature doesn't operate. Accordingly the mode switch program may be required to accommodate the HOCM program.

One way to do this is illustrated in these flow charts. If a patient required this change in operating flow so that HCOM took precedent over mode switching, the tables for parameter priority should be modified. In Table 3.

The MS priority for SAV (AV interval after an atrial sense) and PAV (AV interval after an atrial pace) is for both 1 and HOCM it is 2 and 3, respectively. In Table 4 the priorities are reversed. (An "na"" means priorities for this therapy program are not applicable).

Alternatively, the mere change of table priorities from these in Table 3 to those in Table 4, without modifying the flow chart order in FIG. 5a can be accomplished by modifying the HOCM program to apply to historical SAV and PAV if a mode switch has occurred.

Of course it may be noted that each therapy feature program could store its own priority and a coordination program could assemble them in a coordinated structure but an index or table which each therapy program can access seems preferable as a simple approach.

TABLE 3

| escI/VAI/SAV/PAV/PVAPP | | | | | |
|---|---|---|---|---|---|
| A | | | | | na |
| B | | | | | na |
| C | | | | | na |
| D | | | | | na |
| E | | | | | na |
| F | | | | | na |
| MS | 1 | 1 | 1 | 1 | 2 |
| HOCM | | | 3 | 2 | |

TABLE 4

| escI/VAI/SAV/PAV/PVARP | | | | | |
|---|---|---|---|---|---|
| A | | | | | na |
| B | | | | | na |
| C | | | | | na |
| D | | | | | na |
| E | | | | | na |
| F | | | | | na |
| MS | 1 | 1 | 2 | 2 | 2 |
| HOCM | | | 1 | 1 | |

Although a specific embodiment of the invention has been described herein in detail, this has been done only for the purposes of illustrating various aspects of the invention, and is not intended to be limiting with respect to the scope of the invention. It is contemplated that numerous substitutions, alterations, and/or modifications can be made to the disclosed embodiment of the invention without departing from the spirit and scope of the invention as defined in the appended claims.

What is claimed:

1. A method of operating a cardiac pacemaker having at least two pacing therapy features wherein said pacing therapy features can be active simultaneously and when active simultaneously said simultaneously active pacing therapy features are then capable of causing a common operational parameter of the pacemaker to be periodically adjusted during a parameter adjustment cycle, comprising the steps of:

(a) assigning a relative priority to each of said at least two pacing therapy features; and (b) during said parameter adjustment cycle, if said common operational parameter is adjusted in accordance with one of said at least two pacing therapy features, preventing adjustment of said common operational parameter in accordance with any features of lower priority than said one of said at least two pacing therapy features during said each cycle.

2. The method of in accordance with claim 1, wherein said at least two pacing therapy features are selectively activatable.

3. The method of in accordance with claim 1, wherein said common operational parameter is an Escape Interval parameter.

4. The method of claim 1 wherein said common operational parameter is an A-V Delay.

5. The method of claim 1, further comprising operating one said parameter adjustment cycle during each cardiac cycle.

6. The method of claim 1, wherein said at least two pacing features include a Rate Responsive feature with any pacing therapy feature of lower priority than said one pacing thereby feature.

7. An implantable medical device comprising a memory for maintaining parameters of variable value called operational parameters said operational parameters being accessible to a set of pacing therapy features of said implantable medical device that can access said parameters to cause said operational parameters to change in value if at least one of said set of therapy feature determines a change in one of said operational parameter values is warranted and wherein said chance can be made during a periodic parameter adjustment cycle, wherein if a quality of operation of at least two of said set of pacing therapy features depends on said operational parameter value then such said common operational parameter is a common operational parameter considered shared by said at least two pacing therapy features, and wherein said implantable medical device comprises;

a pacing output circuit for generating cardiac stimulating pulses in response to pacing trigger signals;

a pacing program responsive to said values of said common operational parameters accessible to said pacing program;

control circuitry, coupled to said pacing output circuit, for issuing said pacing trigger signals in accordance with said pacing program, sensing circuitry, coupled to said control circuitry, for generating sensing signals indicative of detection of cardiac electrical events; wherein said implantable medical device pacing program further comprises:

algorithmic means for managing access to said common operational parameter by said at least two of said pacing therapy features wherein said management includes limiting access of said at least two pacing therapy features to said common operational parameter;

and wherein said at least two pacing therapy features are managed by said pacing program wherein said at least two pacing therapy features have relative priority with respect to one another, wherein during each parameter adjustment cycle, if said common operational parameter is accessed and changed by a first of said at least two pacing therapy features, change of said common operational parameter by any other than said first of said at least two pacing therapy features of a lower relative priority is not permitted.

8. The cardiac pacemaker of claim 7, further comprising means for selectively activating said at least two pacing therapy features.

9. The cardiac pacemaker of claim 7, wherein said common operational parameter is a sensed A-V Delay parameter.

10. The cardiac pacemaker of claim 7, wherein said common operational parameter is a paced A-V Delay parameter.

11. The implantable medical device of claim 7, further comprising means to determine that a cardiac cycle has occurred, and wherein one said parameter adjustment cycle occurs during each cardiac cycle.

12. An implantable pulse generator system, comprising:
a memory accessible to a control circuit,
a control circuit, responsive to allow adjustments to a predetermined therapeutic parameter and to a common operational parameter during parameter adjustment cycles and to generate pulse generator trigger signals in accordance with variable values in said memory, said variable values being of said predetermined therapeutic parameter and said common operational parameter, and wherein said control circuit is operable to adjust said common operational parameter and wherein said common parameter is used to control a pacing algorithm, said pacing algorithm comprising at least two therapy features for periodically causing said control circuit to adjust said common parameter,
wherein said at least two therapy features have relative priority with respect to one another, wherein, for each parameter adjustment cycle, if said common operational parameter is adjusted in accordance with one of said at least two therapy features, adjustment of said common operational parameter by any of said at least two therapy features having lower priority than said one feature does not occur.

13. The implantable pulse generator system in accordance with claim 12, wherein said at least two therapy features are selectively activatable.

14. The method of operating a pulse generator having at least two therapy features capable of causing a common parameter of the pulse generator to be periodically adjusted during a parameter adjustment cycle, comprising the steps of:

(a) assigning a relative priority to each said at least two therapy features; and (b) during said parameter adjustment cycle, if said common operational parameter is adjusted in accordance with one of said at least two features, not permitting adjustment of said common operational parameter in accordance with any feature of lower priority than said one feature.

15. The method of claim 14, wherein said at least two therapy features are selectively activatable.

16. The method of claim 14, wherein said pulse generator is body-implantable.

17. An implantable medical device having a cardiac pacemaker, said implantable medical device comprising;
memory means for storing a value for a common parameter and programs for controlling the pacemaker comprising a set of pacing therapy feature programs,
at least some of said set of pacing therapy feature programs comprising requests to chance said common parameter value,
a memory for storing a predetermined priority level value for at least two therapy feature programs of said at least some of said set of therapy feature proarams, said priority level value relating said at least two therapy feature programs to said common parameter,
and a coordinating program for coordinating change in said value for said common parameter responsive to requests for change in said common parameter value by said at least two of said pacing therapy feature programs, said coordinating program comprising:
checking means for discovering said priority level value of a first of said at least two therapy feature program requests and,
access to common parameter control means to deny access by said first one of said at least two of said therapy feature programs to said common parameter if said common parameter has already been modified by another of said at least two therapy feature programs discovered by said checking means to have a higher priority level in said memory than said first one of said at least two therapy feature programs.

18. The implantable medical device of claim 17 wherein said memory stores a set of priority values in a table.

19. The implantable medical device of claim 17 having value generating means for generating values called measured variables and for generating values called actions taken data, and further comprising;
histogram data storage means for storing histogram data in said memory means, said histogram data stored in said histogram data storage means comprising said measured variable values and said actions taken values produced by said value generating means,
lockout override means for making automatic adjustments to said predetermined priority level value in said memory based on a review of said histogram data, and for enabling adjustments to said priority value in said memory based on said review being consistent with adjustment criteria.

20. The implantable medical device of claim 19 and comprising means for invoking therapy features and wherein one of said therapy feature programs is called a Pacemaker Mediated Tachycardia(PMT) intervention therapy feature and has a priority level and wherein said histogram data contains an actions taken value representing a number of occurrences per unit time said PMT Intervention therapy feature has been invoked and wherein said adjustment criteria is consistent with said histogram data, then said lockout-override changes said priority value for said PMT intervention therapy feature.

21. The implantable medical device as set forth in claim 19 having a program control means for controlling a flow of activation from one therapy feature program to another.

22. The implantable medical device of set forth in claim 21 wherein said program flow control means is a pointer at a location in each therapy feature program which points to the start of all next possible therapy feature programs.

23. The device of claim 21 wherein said implantable medical device wherein said pacemaker can be activated to provide rate responsiveness and further comprises modality means for maintaining a mode value indicating a current mode of operation of said pacemaker describable by rate responsiveness activation or lack of activation of said rate responsiveness said modalities further indicating whether the pacemaker is pacing or sensing with respect to cardiac chambers of a heart and further wherein said means for program flow control limits therapy feature program activation to only those therapy feature programs that can be effective in said current pacemaker mode.

24. The implantable medical device of claim 23 wherein said set of available feature programs can be modified by a programmer device so as to include or exclude feature therapy programs.

25. The device of claim 23 wherein said program flow control means is accessible by a programmer external to said device, and wherein said set of therapy feature programs can be modified by said program flow control means if said program flow control means is accessed by said programmer device wherein said modified set of therapy feature programs is modified by said access by said programmer to include or exclude therapy feature programs from said set of therapy feature prourams and wherein priority level values related to said therapy feature programs, can also be modified by said programmer.

26. The device of claims 18–20, 21, 22 or 23, wherein said Therapy Feature Programs (TFP) comprise a plurality of TFP's in the set: Rate Response TFP, Ventricular Threshold Tracking TFP, PVC Response TFP, PMT Intervention, TFP, Mode Switching TFP, Rate Drop Response TFP, Sinus Preference TFP, Rate Adaptive AV Delay TFP, Adaptive AV interval TPF, AV Delay Hysteresis TFP, HOCM AV Delay TFP, A—A Timing TFP, Sensor Varied PVARP TFP, and Auto PVARP TFP.

* * * * *

UNITED STATES PATENT AND TRADEMARK OFFICE
CERTIFICATE OF CORRECTION

PATENT NO. : 6,058,326
DATED : May 2, 2000
INVENTOR(S) : Hess and Juran

It is certified that error appears in the above-identified patent and that said Letters Patent is hereby corrected as shown below:

<u>Column 18,</u>
Line 33, delete "thereby feature", replace with -- therapy feature --.
Line 42, delete "chance can be" replace with -- change can be --.

<u>Column 20,</u>
Line 7, delete "comprising requests to chance", replace with -- comprising request to change --.

Signed and Sealed this

Eighteenth Day of January, 2005

JON W. DUDAS
*Director of the United States Patent and Trademark Office*